(12) United States Patent  
Pierce et al.

(10) Patent No.: US 8,439,777 B2  
(45) Date of Patent: May 14, 2013

(54) SCENT DISPERSING APPARATUS

(75) Inventors: William Fred Pierce, DeQuincy, LA (US); Tony James Latiolais, St. Martinville, LA (US)

(73) Assignee: Rac Em Bac, L.L.C., DeQuincy, LA (US)

( * ) Notice: Subject to any disclaimer, the term of this patent is extended or adjusted under 35 U.S.C. 154(b) by 194 days.

(21) Appl. No.: 12/928,772

(22) Filed: Dec. 16, 2010

(65) Prior Publication Data  
US 2012/0153036 A1 Jun. 21, 2012

(51) Int. Cl.  
*F42B 6/04* (2006.01)

(52) U.S. Cl.  
USPC .......................................... 473/578; 473/581

(58) Field of Classification Search ............ 473/578, 473/581  
See application file for complete search history.

(56) References Cited

U.S. PATENT DOCUMENTS

| 4,463,953 | A | * | 8/1984 | Jordan ......................... 473/581 |
|---|---|---|---|---|
| 5,123,567 | A | | 6/1992 | Anderson |
| 5,836,842 | A | | 11/1998 | McLearan |
| 6,174,251 | B1 | | 1/2001 | Lemote |
| 6,450,905 | B1 | | 9/2002 | Edlund |
| 7,601,084 | B2 | | 10/2009 | Martin |
| 2008/0051231 | A1 | | 2/2008 | Everett |
| 2010/0031945 | A1 | | 2/2010 | Shaffer et al. |

* cited by examiner

*Primary Examiner* — John Ricci  
(74) *Attorney, Agent, or Firm* — Schultz & Associates, P.C.

(57) ABSTRACT

An animal attractant, such as a liquid scent can be dispersed from a soft-shelled frangible capsule by positioning the capsule in an enclosure and then attaching the enclosure to an arrow. A plunger secured to the enclosure slidably moves inside the enclosure and causes rapture of the capsule upon impact of the plunger with a solid surface. The liquid animal attractant is dispersed through cutouts formed in the enclosure in a fan-like fashion.

19 Claims, 3 Drawing Sheets

SCENT DISPERSING APPARATUS

BACKGROUND OF THE INVENTION

This invention relates to hunting equipment, and more particularly to an apparatus for dispersing liquid scent substance, such as a deer attractant.

In the sport of game hunting it is conventional for a hunter to select a spot believed to be in a path or other area where the game is likely to be and wait for the animal in a tree or other hiding place. Typically, a hunting stand is erected on a tree above the expected travel path of the animals where a hunter can stay without scaring the animal and without leaving a human scent. To improve the hunter's odds, an attractant such as the scent of such animal may be left in the area so that other animals of the species would investigate it and while doing so, offer more target opportunities for the hunter.

Furthermore, the hunter hiding in a tree has to descend to the ground and spread the scent manually in the target area. A conventional alternative was to wet a rag or other absorbent material, tie the rag to an arrow and then fire the arrow from the tree stand. However, such approach suffers from major disadvantages—the liquid can be spilled on the hunter or his clothes. Moreover, some of the scent is dispersed during the arrow flight and very little of the liquid reaches the ground.

To solve this problem, the sporting industry developed several solutions, some of which is to use an arrow with pre-loaded scent containers. The containers are designed to open or break upon impact with the ground and dispense the liquid scent onto an absorbent medium positioned on the hollow cavity of an arrow. However, the use of absorbent medium necessarily diminishes the amount of scent dispersed in the desired area, thus requiring more than one arrow to be fired in order to establish an attractive site for the animal.

The present invention contemplates elimination of drawbacks associated with conventional scent dispersing arrows and provision of an arrow suitable for accommodating a frangible container that will break or rupture upon impact with the ground.

SUMMARY OF THE INVENTION

It is, therefore, an object of the present invention to provide a scent dispersing arrow for use in game hunting.

It is another object of the invention to provide a scent dispersing arrow that causes a scent container to be penetrated by a plunger, thus dispersing the liquid scent in the desired hunting area.

It is a further object of the invention to provide a scent dispersing arrow that is configured to carry a frangible scent container and a plunger for breaking the scent container upon contact of the arrow with the ground.

These and other objects of the invention are achieved through a provision of a scent dispersing apparatus, comprising a scent dispersing assembly configured for attachment to an arrow. The scent dispersing assembly comprises a scent capsule enclosure and a plunger configured for slidable engagement with the scent capsule enclosure. The scent capsule enclosure comprises a generally hollow body having a pair of opposing cutouts through which an animal attractant, such as liquid scent can exit the hollow body. The hollow body is configured to retain a frangible liquid-scent containing capsule. The plunger is configured to slide into the scent capsule enclosure and cause rapture the scent-containing capsule upon impact of the plunger with a solid surface, such as ground, rock or tree limb.

BRIEF DESCRIPTION OF THE DRAWINGS

Reference will now be made to the drawings, wherein like parts are designated by like numerals, and wherein.

DETAIL DESCRIPTION OF THE INVENTION

Figure 2:
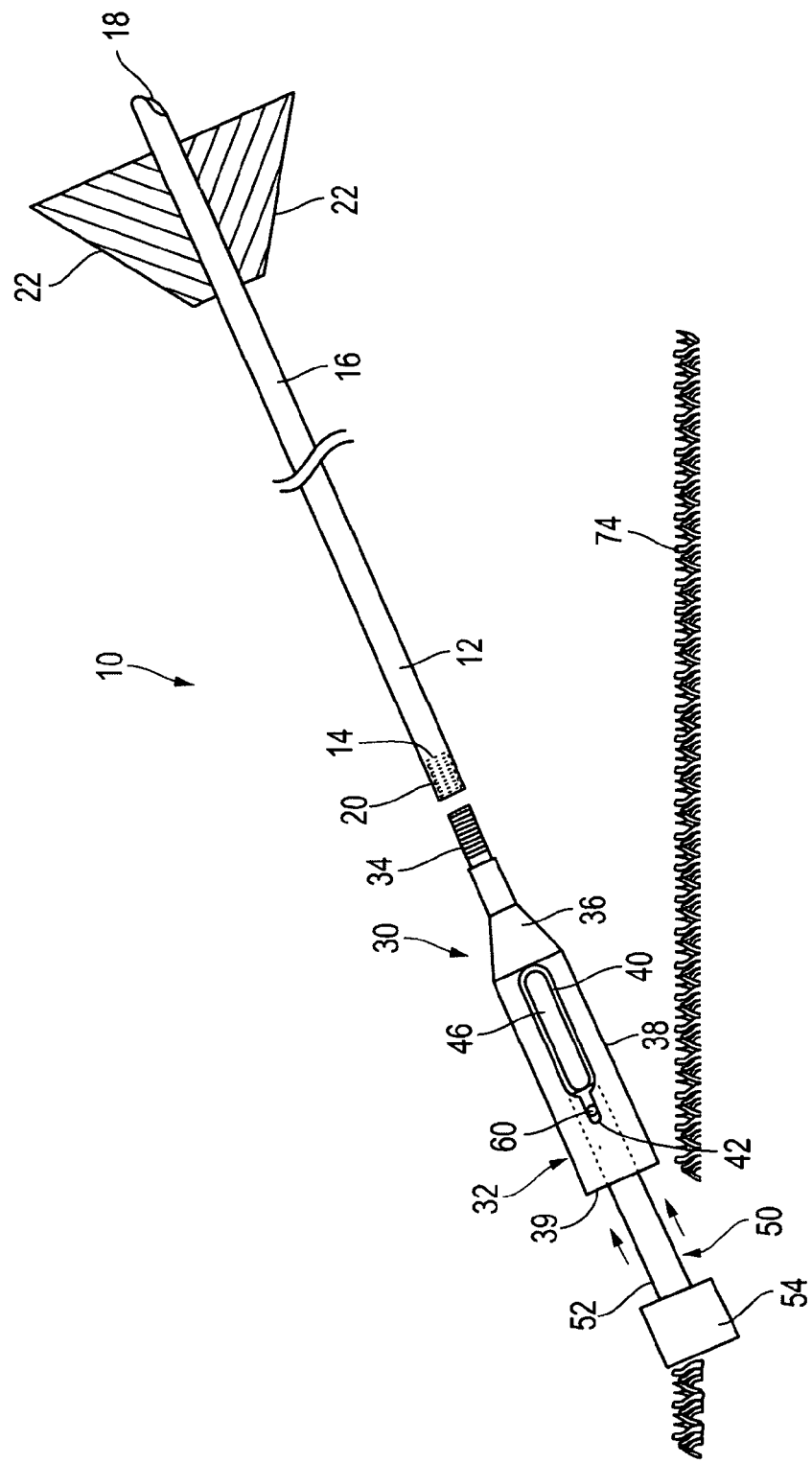
FIG. 2 is a broken-away view of the scent dispersing arrow of the present invention.
Figure 3:
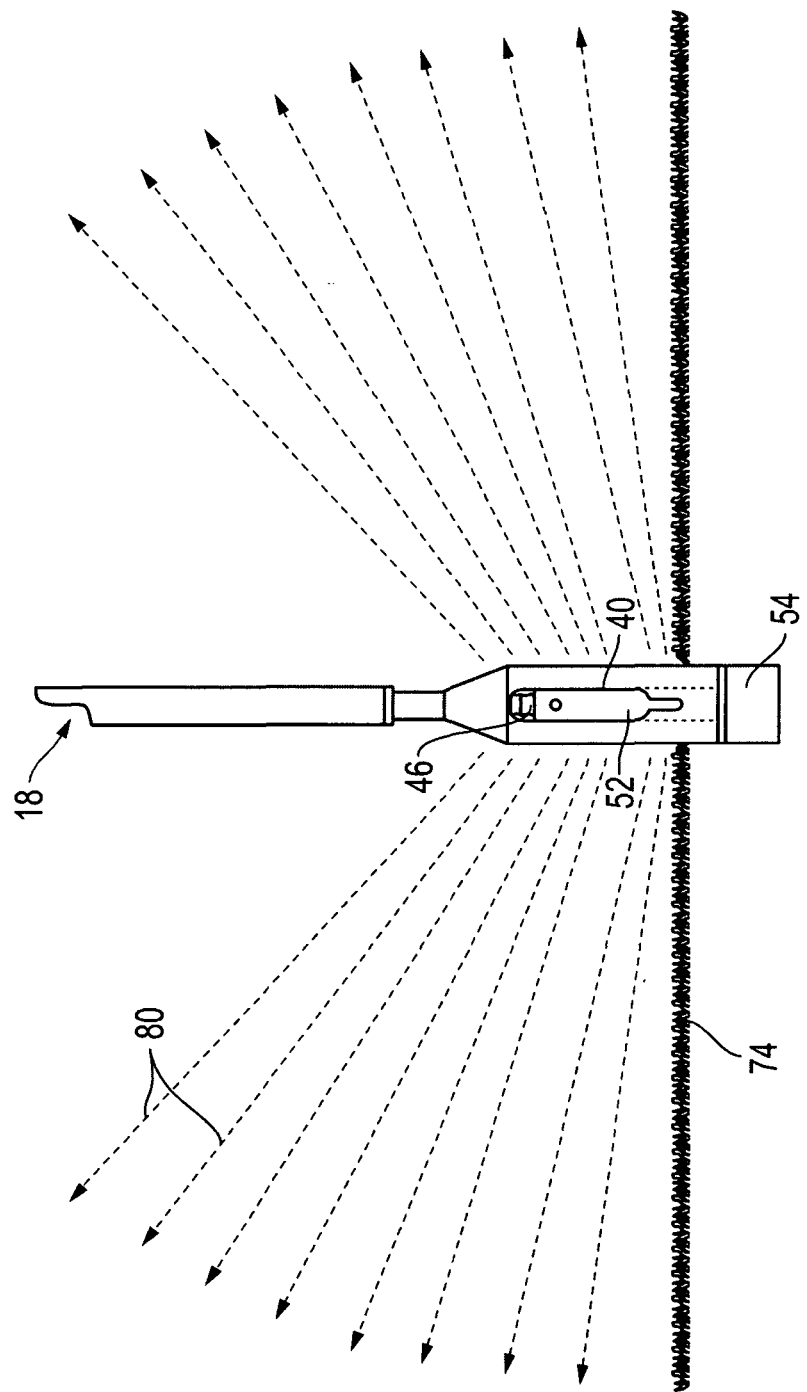
FIG. 3 is a schematic view illustrating fan-like scent dispersing when the arrow impacts the ground.

Turning now to the drawings in more detail, numeral 10 designates the scent dispersing arrow in accordance with the present invention. The arrow 10 comprises an elongate cylindrical shaft 12. The arrow shaft 12 has an open forward end 14 and a closed distant end 16. A nock 18 is formed in the distant end 16 to accommodate a bow string. The forward end 14 of the shaft 12 is open and a threaded insert 20 is positioned therein. Conventional vanes 22 (FIG. 2) may be attached to the arrow shaft 12 adjacent the distant end 16. The arrow 10 may have two or three vanes 22 equidistantly spaced about the circumference of the arrow shaft 12. In one aspect of the invention, the arrow shaft 12 may be formed without the vanes 22, as shown in FIG. 3.

A scent dispersing assembly 30 is detachably secured on the arrow shaft 12. The scent dispersing assembly comprises a housing 32 having a proximate threaded portion 34. The threads of the proximate portion are configured to matingly detachably engage with the threads of the insert 20. The housing 32 also comprises a middle portion 36, which can be formed as a truncated cone, as a transitional member between the proximate threaded portion 34 and a capsule enclosure 38.

The capsule enclosure 38 is formed as a generally cylindrical hollow member having a diameter greater than the threaded portion 34. Of course, the housing 32 can be formed as a cylindrical body having the same diameter from one end to the other, with one end having external threads similar to the threads on the threaded portion 34. In one aspect of the invention, the capsule enclosure 38 and the conical middle portion 36 are formed hollow with an internal chamber formed therein. The capsule enclosure 38 has an open end 39 opposite the threaded portion 34.

The capsule enclosure 38 is provided with a pair of cutouts 40 (only one such cutout is shown in the drawings). The second cutout 40 is formed at a diametrically opposite location in the wall of the capsule enclosure 38. A pair of opposing slots 42 is formed in the wall of the capsule enclosure 38 in open communication with the cutout 40 (only one such slot can be seen in the drawings). The slots 42 are configured to accommodate a stop pin, as will be described in more detail hereinafter. The cutouts 40 do not extend over the entire length of the capsule enclosure 38.

A capsule 46 containing liquid scent is positioned in the capsule enclosure 38. The capsule 46 is formed as a soft-shelled capsule. The capsule 46 can be made from aqueous solutions of gelling agents, such as animal protein (gelatin) or plant polysaccharides of other derivatives like carrageenans and modified forms of starch and cellulose. It is envisioned that the capsule 46 is sized to retain about 1000 mg of synthetic or natural scent. The capsule 46 is at least greater in size than the cutouts 40 to prevent the capsules from falling out of the capsule enclosure 38.

The scent dispersing assembly further comprises a plunger 50 configured to slidably engage the scent enclosure 38 by fitting into the open end 39 of the scent enclosure 38. The plunger 50 comprises an elongate cylindrical contact member 52 and a cap 54. The contact member 52 has a generally cylindrical configuration sized and shaped to fit within the chamber formed in the scent enclosure 38. A concave groove 56 is formed in the contact end 57 of the contact member 52. The cap 54 has a diameter greater than the diameter of the contact member 52. In one aspect of the invention, a concave indentation 55 is formed in an outer end 58 of the cap 50.

A stop member 60 is secured on the exterior of the contact member 52 adjacent the contact end 57 to prevent disengagement of the plunger 50 from the scent capsule enclosure. The stop member 60 may be formed as a pair of opposing pins extending outwardly from the exterior of the contact member 52. The pins of the stop member 60 extend in diametrically opposite directions. The pins are configured to fit within the slots 42 when the contact member is partially inserted into the capsule enclosure 38, as shown in FIG. 2. The stop member 60 can be formed as a pair of deformable bendable resilient pins that bend as the contact member is positioned in the scent enclosure 38 and then spring outwardly from the contact member 52 as the pins push into the slots 42. When the hunter wishes to remove the plunger 50 from the scent enclosure, the hunter rotates the plunger 90 degrees to move the pins out of engagement with the slot 40 and pulls the plunger outwardly.

The scent enclosure 38 and the plunger 50 can be made from a variety of materials, such as stainless steel, aluminum and the like. The arrow shaft can be made of rigid plastic or other conventional material. It is envisioned that the scent dispersing assembly 30 can be manufactured and sold separately from the arrow 12, and can be adapted for use with any type of arrow. A kit containing the scent dispersing assembly 30 and a plurality of scent-containing capsules 46 can be sold as a separate item.

In operation, a hunter 70 is positioned in a tree stand 72, which is elevated above ground 74. Usually, the tree stand 72 is erected in a location adjacent a food plot 75 or trail 76 frequented by the animals, such as deer. Preferably, the area around the tree 73 where the tree stand is positioned contains minimal human scent that can be discerned by the hunted animal. The hunter 70 withdraws the plunger 50 from its engagement with the capsule enclosure 38. The hunter then positions one scent-containing capsule 46 into the capsule enclosure, pushing the capsule into the inner chamber until at least a portion of the capsule is positioned within the cutouts 40. The hunter 70 then pushes the plunger 50 into the capsule enclosure making sure that the end 57 of the contact member 52 contacts the capsule 46. If necessary, the hunter 70 twists the plunger until the pins of the stop member 60 engage within the slots 42 and protrude partially therefrom. A portion of the contact member 52 will remain outside of the scent enclosure 38, as shown in FIG. 2.

Figure 1:
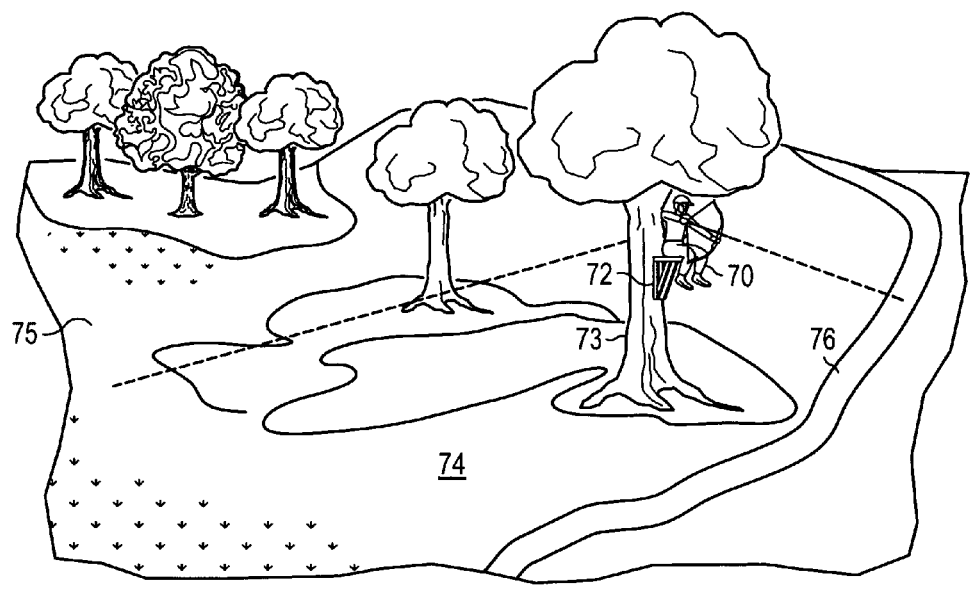
FIG. 1 is a schematic view of the hunting location where the scent dispersing arrow of this invention is used.
Figure 4:
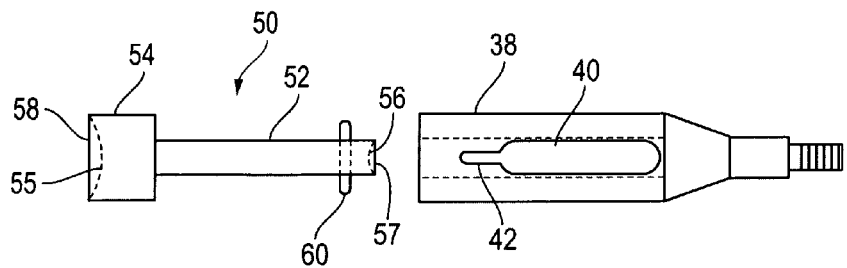
FIG. 4 is a detail view of the cap and plunger assembly of the present invention.

The hunter 70 then threadably engages the scent dispersing assembly 30 with the arrow shaft 12 using the matching threads 20 in the shaft 12 and the external threads on the threaded portion 34. Once the scent dispersing assembly 30 is securely engaged with the arrow shaft 12, the hunter fires the arrow aiming either toward the food plot 75 or to a trail 76. The trajectory of the arrow flight is shown in phantom lines in FIG. 1.

As the arrow hits the ground 74 with the cap 54, the plunger 50 is forced to move axially within the capsule enclosure 38 into a contact with the capsule 46. A similar effect can be achieved by causing the plunger to come into contact with any other hard object, such as a stone or tree branch. The forceful impact of the plunger with a solid surface transmits the impact force to the capsule.

As the plunger impacts the solid surface, the contact member moves into the enclosure 38, deforms the soft-shelled capsule 46 and causes the frangible capsule to break or burst. As a consequence the liquid scent exits the capsule 46 in a fan-like fashion through opposing cutouts 40 formed in the capsule enclosure 38. The dispersal of the liquid scent is schematically shown by phantom lines 80 in FIG. 3. The plunger 52 is forced deeper into the opening formed in the capsule enclosure 38, while the enlarged diameter cap 54 stops the plunger 52 when it contacts the end 39 of the capsule enclosure 38.

Following the hunt, the hunter 70 can retrieve the arrow, disengage the plunger from the capsule enclosure 38 and load another capsule with liquid scent into the capsule enclosure 38. The assembly 30 can thus be used numerous times.

The scent dispersing arrow and the scent dispersing assembly of the present invention prevent spills of the liquid scent on the hunter or hunter's closing by using an encapsulated item. The hunter can select the most advantageous point for scent dispersal from an elevated position, without leaving undesirable human scent on the deer trail. The targeted delivery of the liquid scent to the most desired area ensures maximum exposure thereof to the game.

Many changes and modifications can be made in the design of the present invention without departing from the spirit thereof. I, therefore, pray that my rights to the present invention be limited only by the scope of the appended claims.

We claim:

1. A scent dispersing apparatus, comprising:
   a scent capsule enclosure with a threaded end for detachable engagement with an arrow and an open end configured to receive a plunger;
   the scent capsule enclosure further comprising a generally hollow body with a pair of opposing cutouts, where the body is configured to retain a soft-shelled capsule;
   the capsule containing liquid scent animal attractant;
   the plunger slidably engaged with the scent capsule enclosure; and
   wherein upon impact of the plunger with a solid surface, the plunger slides into the body thus rupturing the capsule and releasing the liquid scent animal attractant.

2. The apparatus of claim 1, wherein said plunger comprises an elongate contact member configured for slidable movement within the scent capsule enclosure and an enlarged cap secured on a free end of the contact member.

3. The apparatus of claim 2, wherein the contact member is provided with a means for preventing disengagement of the plunger from the scent capsule enclosure.

4. The apparatus of claim 3, wherein said means for preventing disengagement of the plunger from the scent capsule enclosure comprises a pair of opposing pins secured on exterior of the contact member and extending outwardly therefrom.

5. The apparatus of claim 4, wherein said scent capsule enclosure is provided with a pair of opposing slots, each slot being configured to receive one of the opposing pins therein when the plunger is engaged with the scent capsule enclosure.

6. The apparatus of claim 4, wherein each of said opposing pins is formed from a flexible bendable resilient material.

7. A scent dispersing apparatus, comprising:
   an elongated arrow shaft having a first end provided with threads;
   a scent capsule enclosure having a threaded end configured for detachable engagement with the first end of the arrow shaft, said scent capsule enclosure comprising a hollow body formed with a pair of opposing cutouts;
a plunger comprising a contact member configured for slidable engagement with the hollow body; and
a frangible soft-shelled capsule containing an animal attractant, said capsule being configured to fit within the hollow body and be fractured by the contact member upon forceful impact of the plunger with a solid surface releasing the animal attractant.

8. The apparatus of claim 7, wherein said plunger comprises an enlarged cap secured on a free end of the contact member, said enlarged cap limiting sliding movement of the contact member within the hollow body.

9. The apparatus of claim 7, wherein the contact member is provided with a means for preventing disengagement of the plunger from the hollow body.

10. The apparatus of claim 9, wherein said means for preventing disengagement of the plunger from the hollow body comprises a pair of opposing pins secured on exterior of the contact member and extending outwardly therefrom.

11. The apparatus of claim 10, wherein said hollow body is provided with a pair of opposing slots, each slot being configured to receive one of the opposing pins therein when the plunger is engaged with the hollow body.

12. A method of dispersing an animal attractant, comprising the steps:
providing a frangible capsule containing a liquid animal attractant;
providing a scent dispersing assembly configured for attachment to an arrow, said scent dispersing assembly comprising a scent capsule enclosure and a plunger configured for slidable engagement with the scent capsule enclosure, said scent capsule enclosure comprising a generally hollow body having a pair of opposing cutouts;
positioning the capsule in the hollow body such that at least a portion of the capsule is exposed through the opposing cutouts;
engaging the plunger with the hollow body;
securing the scent dispersing assembly with an arrow;
firing the arrow and causing the plunger to impact a solid surface, thereby forcing the plunger into forceful contact with the frangible capsule;
causing the frangible capsule to break and disperse the animal attractant from the hollow housing.

13. The method of claim 12, wherein said hollow body is provided with threads configured for engagement with the arrow.

14. The method of claim 12, wherein said capsule is a soft-shelled capsule.

15. The method of claim 12, wherein the animal attractant is caused to disperse from the hollow body through the cutouts in a fan-like manner.

16. The method of claim 12, wherein said plunger comprises an elongated contact member slidably engageable with the hollow body and an enlarged cap secured on a free end of the contact member, said enlarged cap limiting sliding movement of the contact member within the hollow body.

17. The method of claim 16, wherein the contact member is provided with a means for preventing disengagement of the plunger from the hollow body.

18. The method of claim 17, wherein said means for preventing disengagement of the plunger from the hollow body comprises a pair of opposing pins secured on exterior of the contact member and extending outwardly therefrom.

19. The method claim 18, wherein said hollow body is provided with a pair of opposing slots, each slot being configured to receive one of the opposing pins therein when the plunger is engaged with the hollow body.

\* \* \* \* \*